United States Patent
Zhao et al.

(10) Patent No.: US 12,409,246 B2
(45) Date of Patent: Sep. 9, 2025

(54) AROMA DIFFUSER

(71) Applicant: Zhangzhou iHastek Inc., Fujian (CN)

(72) Inventors: Chaoqiang Zhao, Zhangzhou (CN); Xianfu Lin, Zhangzhou (CN); Rongwei Wu, Zhangzhou (CN)

(73) Assignee: Zhangzhou iHastek Inc., Zhangzhou (CN)

( * ) Notice: Subject to any disclaimer, the term of this patent is extended or adjusted under 35 U.S.C. 154(b) by 472 days.

(21) Appl. No.: 18/079,145

(22) Filed: Dec. 12, 2022

(65) Prior Publication Data

US 2024/0115753 A1    Apr. 11, 2024

(30) Foreign Application Priority Data

Oct. 8, 2022   (CN) .......................... 202211230744.3

(51) Int. Cl.
*A61L 9/14* (2006.01)

(52) U.S. Cl.
CPC ......... *A61L 9/145* (2013.01); *A61L 2209/134* (2013.01)

(58) Field of Classification Search
CPC ....................................................... A61L 9/14
See application file for complete search history.

(56) References Cited

U.S. PATENT DOCUMENTS

| 4,243,396 A * | 1/1981 | Cronenberg .......... A61M 16/16 261/78.2 |
| 2016/0000959 A1 * | 1/2016 | Sevy .......................... A61L 9/14 422/4 |

FOREIGN PATENT DOCUMENTS

CN          112656987 A       4/2021

* cited by examiner

*Primary Examiner* — Donald R Spamer
(74) *Attorney, Agent, or Firm* — Cooper Legal Group, LLC

(57) ABSTRACT

An aroma diffuser comprises a compression plug connected to an air pump, an oil tube, an atomizing chamber, a spray outlet base, and a rotary spray outlet cover. The atomizing chamber comprises a chamber, a spray outlet sleeve, and a spray outlet, a distance between the air outlet and a chamber wall of the atomizing chamber is 11-13 times an aperture diameter of the air outlet, the spray outlet of the atomizing chamber extends downward to form a spray outlet channel, the spray outlet sleeve is sleeved outside of the spray outlet channel, atomized essential oil enters into the gaps between the spray outlet sleeve and the spray outlet channel from the groove notch and is then sprayed out, a bottom of the spray outlet sleeve is obliquely disposed and comprises a first reflux hole, and the rotary spray outlet cover is rotatably connected to the spray outlet base.

11 Claims, 6 Drawing Sheets

AROMA DIFFUSER

RELATED APPLICATIONS

This application claims priority to Chinese patent application number 202211230744.3, filed on Oct. 8, 2022. Chinese patent application number 202211230744.3 is incorporated herein by reference.

FIELD OF THE DISCLOSURE

The present disclosure relates to an aroma diffuser.

BACKGROUND OF THE DISCLOSURE

At present, atomization of most aroma diffusers on the market is performed by sonicating with a transducer. Operating time of essential oil is short, and manufacturing cost is high. Some mechanical atomization structures lack control over an amount of the essential oil that is used, resulting in fast use of the essential oil. Chinese patent application with the publication number of CN112656987A provides an aroma diffuser. The aroma diffuser works according to Bernoulli's principle. Compressed air is accelerated by a compression plug to generate negative pressure, the essential oil in an essential oil bottle is sucked up through an oil tube and blown out to form a spray, and atomized essential oil is sprayed out of a spray outlet to achieve mechanical atomization effects. A blocking structure is disposed at an opening of an air outlet of the aroma diffuser, noise is large, and atomization is insufficient.

BRIEF SUMMARY OF THE DISCLOSURE

The present disclosure provides an aroma diffuser to solve the deficiencies in the background.

In order to solve the technical problem, a technical solution of the present disclosure is as follows.

An aroma diffuser, which comprises a compression plug connected to an air pump, an oil tube, an atomizing chamber, a spray outlet base, and a rotary spray outlet cover. The oil tube and the atomizing chamber are connected to a bottle for receiving essential oil, air ejected from the compression plug is mixed with a liquid of the essential oil derived from the oil tube and then enters into the atomizing chamber through an air outlet, the atomizing chamber comprises a chamber, a spray outlet sleeve disposed in the chamber, and a spray outlet disposed on the chamber, a distance between the air outlet and a chamber wall of the atomizing chamber is 11-13 times an aperture diameter of the air outlet, the spray outlet of the atomizing chamber extends downward to form a spray outlet channel, the spray outlet sleeve is sleeved outside of the spray outlet channel, gaps are respectively disposed between an outer peripheral wall or a bottom of the spray outlet channel and the spray outlet sleeve, an upper part of the spray outlet sleeve comprises a groove notch, atomized essential oil enters into the gaps between the spray outlet sleeve and the spray outlet channel from the groove notch and is then sprayed out from the spray outlet channel and the spray outlet, a bottom of the spray outlet sleeve is obliquely disposed and comprises a first reflux hole at a lowest position, the spray outlet base is disposed on the spray outlet, the rotary spray outlet cover is rotatably connected to the spray outlet base, an atomizing transmitting chamber is formed between the spray outlet base and the rotary spray outlet cover, the spray outlet is communication with the atomizing transmitting chamber, a bottom of the spray outlet base comprises a second reflux hole in communication the atomizing chamber, and the rotary spray outlet cover comprises a spray outlet hole.

In a preferred embodiment, the spray outlet sleeve comprises a spray baffle, and the spray baffle is staggered with the groove notch on a projection in a direction from a top of the spray outlet sleeve to the bottom of the spray outlet sleeve.

In a preferred embodiment, the bottom of the spray outlet base comprise a reflux tube, and the reflux tube is in communication with the second reflux hole and the atomizing chamber.

In a preferred embodiment, a spray transmission plate is disposed in the rotary spray outlet cover below the spray outlet hole, and the spray transmission plate is obliquely disposed relative to the spray outlet hole.

In a preferred embodiment, an upper part of the spray outlet base is an annular wall, and the rotary spray outlet cover comprises an annular groove matched with the annular wall of the spray outlet base.

In a preferred embodiment, an anti-detachment structure is disposed between the rotary spray outlet cover and the spray outlet base.

In a preferred embodiment, the rotary spray outlet cover comprises an elastic snap joint configured to be clamped at the bottom of the spray outlet base.

In a preferred embodiment, the chamber of the atomizing chamber comprises a pillar chamber part at a lower part and a tapered chamber part at an upper part that are connected each other, and the spray outlet is disposed on a tapered top end of the tapered chamber part.

In a preferred embodiment, a sealing structure is disposed between the pillar chamber part and the tapered chamber part.

Compared with the existing techniques, the technical solution has the following advantages.

The present disclosure provides gentle spray without large particles and reduced noise by maintaining the distance between the air outlet and the chamber wall of the atomizing chamber and the aperture diameter of the air outlet at a reasonable ratio, forming an atomizing channel between the spray outlet sleeve and the spray outlet channel, and forming the atomizing transmitting chamber between the spray outlet base and the rotary spray outlet cover. Noise is reduced to less than 43 dB. When the spray is produced, multi-layer reflux is achieved, the operating time of the essential oil is elongated, and rotary spray at 360° can be achieved.

One or more spray baffles are disposed on the spray outlet sleeve, the essential oil is transmitted, and ascending air current is blocked.

The anti-detachment structure is disposed between the rotary spray outlet cover and the spray outlet base, and the structure is reasonable.

The sealing structure is disposed between the polar chamber part and the tapered chamber part to further achieve hermetical sealing performance of the chamber.

DETAILED DESCRIPTION OF THE EMBODIMENTS

Figure 1:
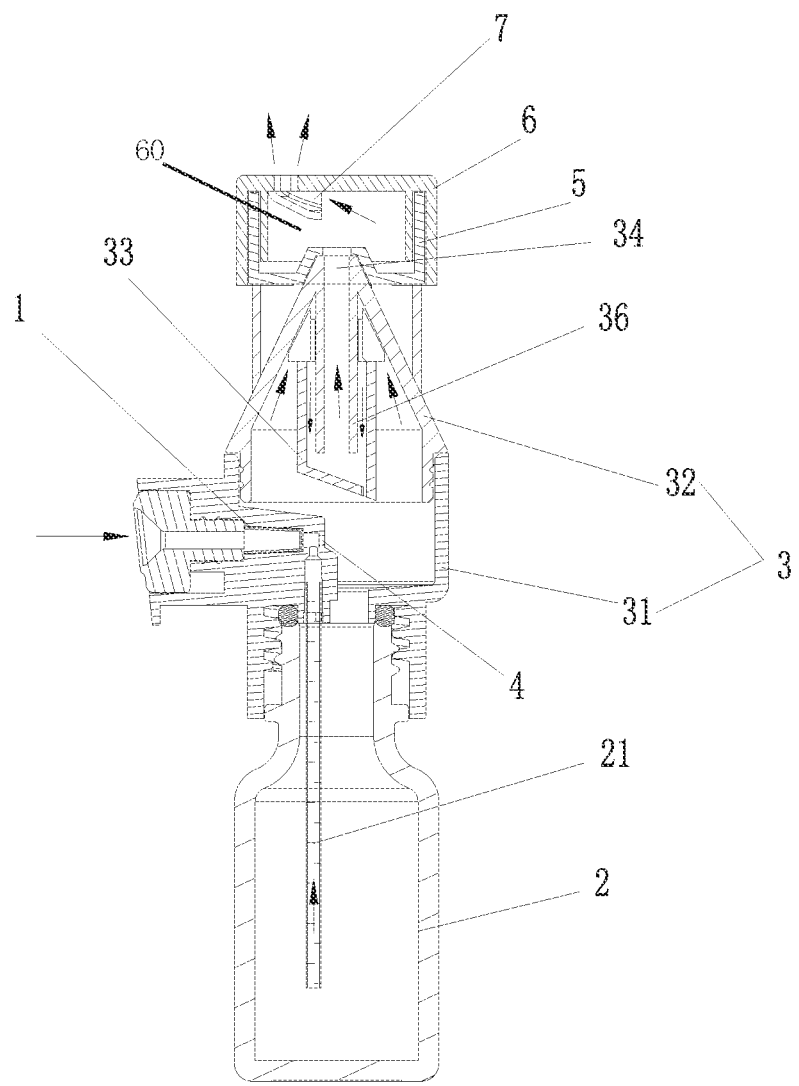
FIG. 1 illustrates a first cross-sectional view of an aroma diffuser of Embodiment 1 of the present disclosure.

The present disclosure will be further described below in combination with the accompanying drawings and embodiments. However, the aroma diffuser of the present disclosure is not limited to the embodiments.

Embodiment 1

Referring to FIGS. 1 to 6, an aroma diffuser of the present disclosure comprises a compression plug 1 connected to an air pump, an oil tube 21, and an atomizing chamber 3 connected to a bottle 2 for receiving essential oil. Air ejected from the compression plug 1 is mixed with a liquid of the essential oil derived from the oil tube 21 and then enters the atomizing chamber 3 through an air outlet 4.

The atomizing chamber 3 comprises a chamber, a spray outlet sleeve tube 33 disposed in the chamber, and a spray outlet 34 disposed on the chamber. In this embodiment, the chamber of the atomizing chamber 3 comprises a pillar chamber part 31 at a lower side and a tapered chamber part 32 (e.g., a conical chamber part) at an upper side that are connected each other. A sealing structure, such as an O-ring 35, is disposed between the pillar chamber part 31 and the tapered chamber part 32.

In this embodiment, a distance between the air outlet 4 and a chamber wall of the chamber (the pillar chamber part 31) of the atomizing chamber is 11-13 times an aperture diameter of the air outlet 4. Therefore, the aroma diffuser in this embodiment can achieve good atomization effects, sufficient atomization, and small atomization particle size.

The spray outlet 34 is disposed on a tapered top end of the tapered chamber part 32. The spray outlet 34 extends downward to form a spray outlet channel 36, and the spray outlet sleeve tube 33 is sleeved outside of the spray outlet channel 36. Referring to FIG. 1, gaps are respectively disposed between an outer peripheral wall or a bottom of the spray outlet channel 36 and the spray outlet sleeve tube 33. Referring in combination with FIGS. 5 and 6, an upper part of the spray outlet sleeve tube 33 comprises two groove notches 331, and middle and lower parts of the spray outlet sleeve tube 33 comprise two spray baffles 332. The two spray baffles 332 and the two groove notches 331 are staggered on a projection surface, and the two spray baffles 332 are used to transmit the essential oil and block ascending air current. Atomized essential oil enters into the gaps between the spray outlet sleeve tube 33 and the spray outlet channel 36 from the two groove notches 331 and is then sprayed out from the spray outlet channel 36 and the spray outlet 34. The bottom of the spray outlet sleeve tube 33 is inclined and comprises a first reflux hole 333 at a lowest position. The aroma diffuser further comprises a spray outlet base 5 and a rotary spray outlet cover 6. The spray outlet base 5 is disposed on the spray outlet 34, and the rotary spray outlet cover 6 is rotatably connected to the spray outlet base 5. The spray outlet base 5 and the rotary spray outlet cover 6 form an atomizing transmitting chamber 60, and the spray outlet 34 is in communication with the atomizing transmitting chamber 60. A bottom of the spray outlet base 5 comprises a second reflux hole 51 in communication with the atomizing chamber 3. The rotary spray outlet cover 6 comprises a spray outlet hole 61, so the rotary spray outlet cover 6 can be rotated to achieve rotary spray within 360° by operation.

Figure 2:
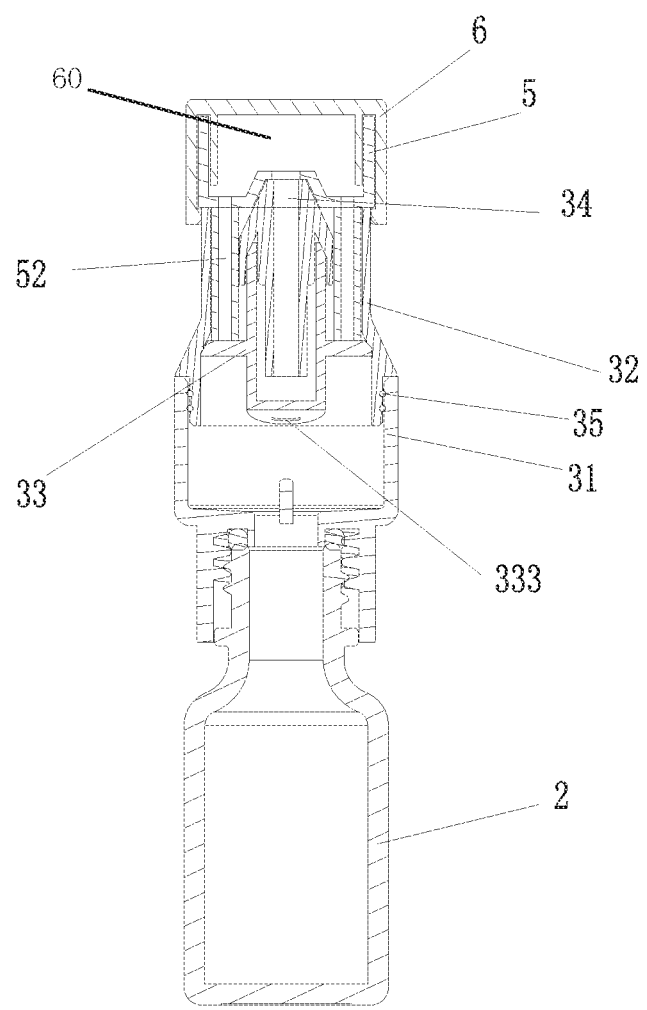
FIG. 2 illustrates a second cross-sectional view of the aroma diffuser of Embodiment 1 of the present disclosure.
Figure 3:
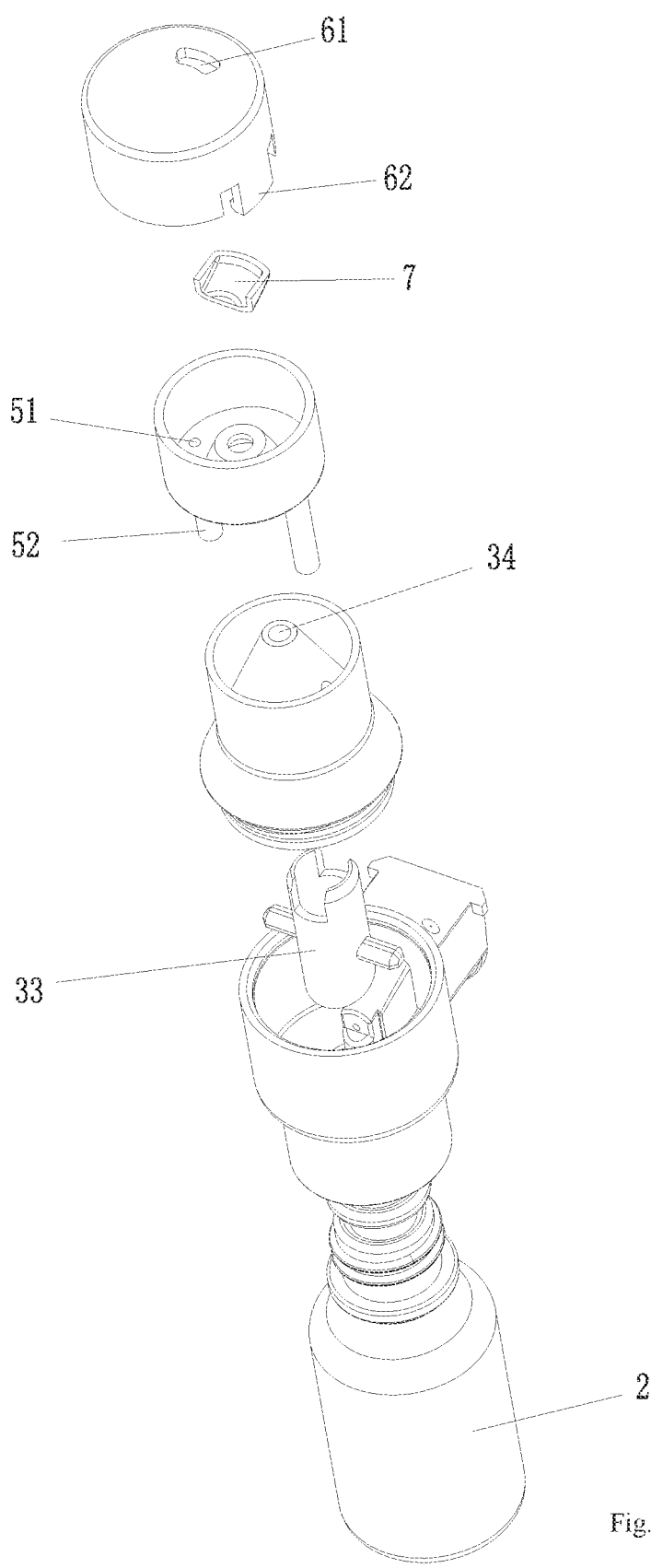
FIG. 3 illustrates an exploded perspective view of the aroma diffuser of Embodiment 1 of the present disclosure.
Figure 4:
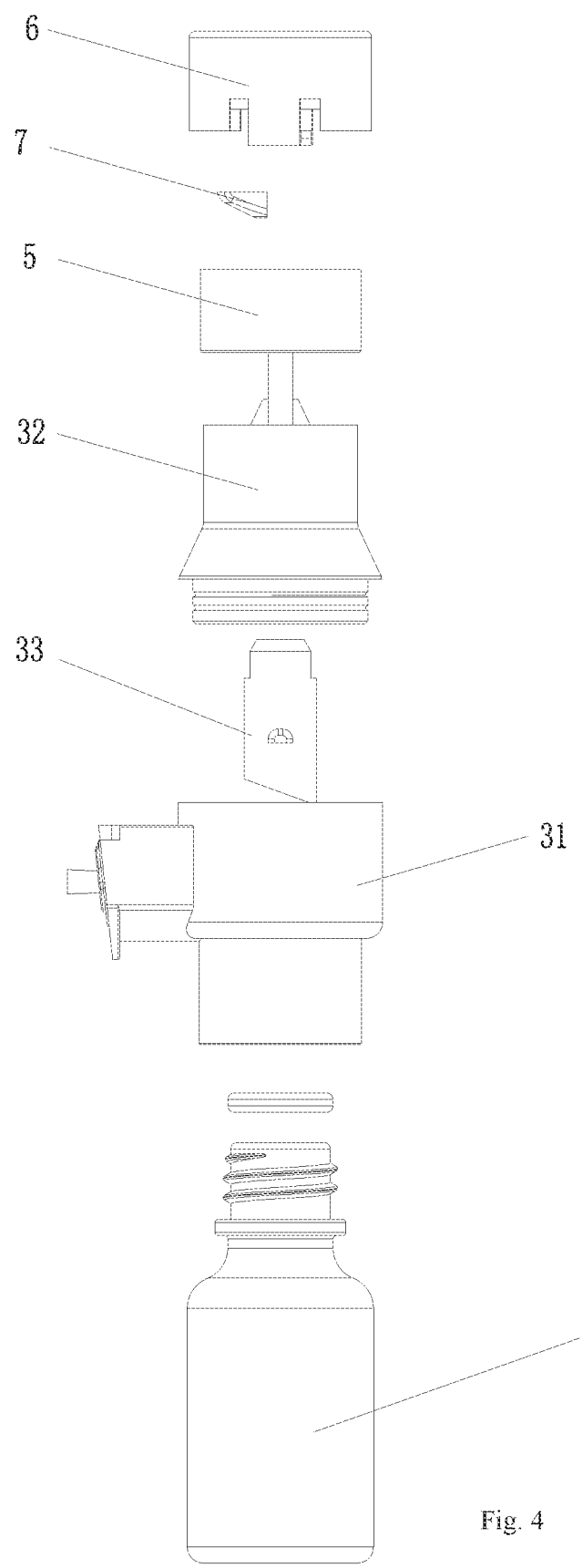
FIG. 4 illustrates an exploded view of a side surface of the aroma diffuser of Embodiment 1 of the present disclosure.
Figure 5:
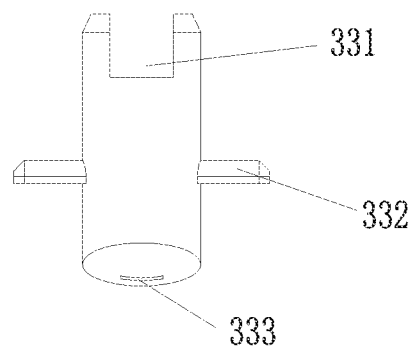
FIG. 5 illustrates a structural view of a spray outlet sleeve tube of the aroma diffuser of Embodiment 1 of the present disclosure.
Figure 6:
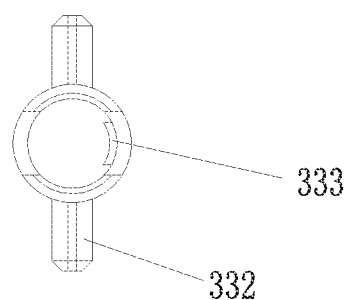
FIG. 6 illustrates a top view of the spray outlet sleeve tube of the aroma diffuser of Embodiment 1 of the present disclosure.

Referring to FIGS. 2 and 3, the bottom of the spray outlet base 5 comprises a reflux tube 52, and the reflux tube 52 is in communication with the second reflux hole 51 and the atomizing chamber 3. Furthermore, a middle of the bottom of the spray outlet base 5 comprises a protrusion that matches a top of the tapered chamber part 32. A bottom wall inside the spray outlet base 5 forms an annular groove, and the second reflux hole 51 is disposed on the annular groove to facilitate recovery and transmission of the essential oil.

A spray transmission plate 7 is disposed in the rotary spray outlet cover 6 below the spray outlet hole 61, and the spray transmission plate 7 is obliquely disposed relative to the spray outlet hole 61 to achieve oblique spray effects.

Specifically, referring to FIGS. 1 and 3, an upper part of the spray outlet base 5 is an annular wall, and the rotary spray outlet cover 6 comprises an annular groove matched with the annular wall of the spray outlet base 5. At the same time, an anti-detachment structure is disposed between the rotary spray outlet cover 6 and the spray outlet base 5. Specifically, the rotary spray outlet cover 6 comprises an elastic snap joint 62 that can be clamped at the bottom of the spray outlet base 5.

Embodiment 2

Figure 7:
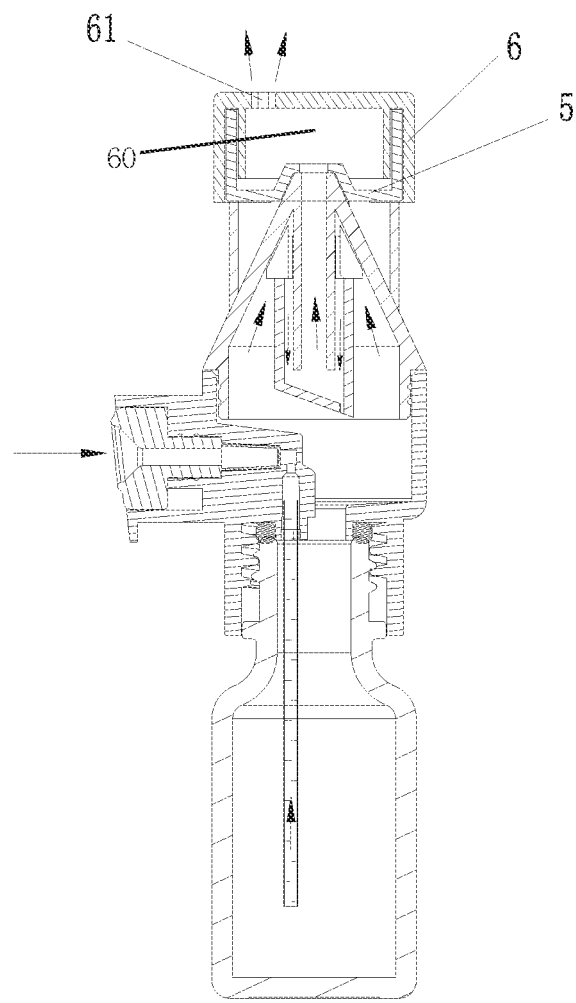
FIG. 7 illustrates a cross-sectional view of an aroma diffuser of Embodiment 2 of the present disclosure.

Referring to FIG. 7, Embodiment 2 differs from Embodiment 1 in that Embodiment 2 is not provided with the spray transmission plate 7, and the spray is directly ejected from the spray outlet hole 61 in the atomizing transmitting chamber 60.

The aforementioned embodiments are merely some embodiments of the aroma diffuser of the present disclosure, and the scope of the disclosure is not limited thereto. Thus, it is intended that the present disclosure cover any modifications and variations of the presently presented embodiments provided they are made without departing from the appended claims and the specification of the present disclosure.

What is claimed is:
1. An aroma diffuser, comprising:
a compression plug connected to an air pump,
an oil tube,
an atomizing chamber,
a spray outlet base, and
a rotary spray outlet cover, wherein:
the oil tube and the atomizing chamber are connected to a bottle for receiving essential oil,
air ejected from the compression plug is mixed with a liquid of the essential oil derived from the oil tube and then enters into the atomizing chamber through an air outlet,
the atomizing chamber comprises a chamber, a spray outlet sleeve disposed in the chamber, and a spray outlet disposed on the chamber,
a distance between the air outlet and a chamber wall of the atomizing chamber is 11-13 times an aperture diameter of the air outlet,
the spray outlet of the atomizing chamber extends downward to form a spray outlet channel, the spray outlet sleeve is sleeved outside of the spray outlet channel, gaps are respectively disposed between an outer peripheral wall or a bottom of the spray outlet channel and the spray outlet sleeve, an upper part of the spray outlet sleeve comprises a groove notch, atomized essential oil enters into the gaps between the spray outlet sleeve and the spray outlet channel from the groove notch and is then sprayed out from the spray outlet channel and the spray outlet, a bottom of the spray outlet sleeve is obliquely disposed and comprises a first reflux hole at a lowest position, the spray outlet base is disposed on the spray outlet, the rotary spray outlet cover is rotatably connected to the spray outlet base, an atomizing transmitting chamber is formed between the spray outlet base and the rotary spray outlet cover, the spray outlet is communication with the atomizing transmitting chamber, a bottom of the spray outlet base comprises a second reflux hole in communication the atomizing chamber, and the rotary spray outlet cover comprises a spray outlet hole.

2. The aroma diffuser according to claim 1, wherein:
the spray outlet sleeve comprises a spray baffle, and
the spray baffle is staggered with the groove notch on a projection in a direction from a top of the spray outlet sleeve to the bottom of the spray outlet sleeve.

3. The aroma diffuser according to claim 1, wherein:
the bottom of the spray outlet base comprise a reflux tube, and
the reflux tube is in communication with the second reflux hole and the atomizing chamber.

4. The aroma diffuser according to claim 1, wherein:
a spray transmission plate is disposed in the rotary spray outlet cover below the spray outlet hole, and
the spray transmission plate is obliquely disposed relative to the spray outlet hole.

5. The aroma diffuser according to claim 1, wherein:
an upper part of the spray outlet base is an annular wall, and
the rotary spray outlet cover comprises an annular groove matched with the annular wall of the spray outlet base.

6. The aroma diffuser according to claim 1, wherein an anti-detachment structure is disposed between the rotary spray outlet cover and the spray outlet base.

7. The aroma diffuser according to claim 1, wherein the rotary spray outlet cover comprises an elastic snap joint configured to be clamped at the bottom of the spray outlet base.

8. The aroma diffuser according to claim 1, wherein:
the chamber of the atomizing chamber comprises a pillar chamber part at a lower part and a tapered chamber part at an upper part that are connected each other, and
the spray outlet is disposed on a tapered top end of the tapered chamber part.

9. The aroma diffuser according to claim 8, wherein a sealing structure is disposed between the pillar chamber part and the tapered chamber part.

10. The aroma diffuser according to claim 5, wherein an anti-detachment structure is disposed between the rotary spray outlet cover and the spray outlet base.

11. The aroma diffuser according to claim 5, wherein the rotary spray outlet cover comprises an elastic snap joint configured to be clamped at the bottom of the spray outlet base.

* * * * *